United States Patent [19]
Jackson

[11] Patent Number: 6,093,827
[45] Date of Patent: Jul. 25, 2000

[54] PROCESS FOR THE PREPARATION OF 10,11-DIHYDRO-5H-DIBENZO[A,D] CYCLOHEPT-5-ENES AND DERIVATIVES THEREOF

[75] Inventor: William Paul Jackson, Twickenham, United Kingdom

[73] Assignee: Rolabo S.L., Barcelona, Spain

[21] Appl. No.: 09/383,078

[22] Filed: Aug. 26, 1999

[30] Foreign Application Priority Data

Feb. 26, 1997 [GB] United Kingdom .................. 9703992
Feb. 26, 1998 [WO] WIPO .................. PCT/GB98/00605

[51] Int. Cl.$^7$ ...................... C07D 211/70; C07D 211/74
[52] U.S. Cl. ...................... 546/194; 546/203
[58] Field of Search ...................... 546/194, 203

[56] References Cited

U.S. PATENT DOCUMENTS 3,905,972   9/1975   Dostert et al. ...................... 546/203 X

FOREIGN PATENT DOCUMENTS 2266676   10/1975   France .
2337706   8/1977   France .

OTHER PUBLICATIONS

Chemical Abstracts, vol. 94, No. 17, Apr. 27, 1981, Columbus, Ohio, US; abstract No. 139113, XP002068291; see abstract & D. Lenoir et al.: J. Chem. Res. Synop., vol. 12, 1980, pp. 396–397.

Chemical Abstracts, vol. 89, No. 15, Oct. 9, 1978, Columbus Ohio, US; abstract No. 128558, XP002068292; see abstract & J.E. McMurry et al. RRY: J. Org. Chem., vol. 43, No. 17, 1978, pp. 3255–3266.

Chemical Abstracts, vol. 101, No. 15, Oct. 8, 1984, Columbus Ohio, US; abstract No. 130367, XP002068293; see abstract & P. Lemmen et al.: Chem. Ber., vol. 117, No. 7, 1984, pp. 2300–2313.

M.M. Cid et al.: Tetrahedron, vol. 44, No. 19, 1988, Oxford GB, pp. 6197–6200, XP002068290, cited in the application, see whole document.

Chemical Abstracts, vol. 84, No. 15, Apr. 12, 1976, Columbus Ohio, US; abstract No. 105080, XP002068294; see abstract & J.E. McMurry et al.: J. Org. Chem., vol. 41, No. 5, 1976, pp. 896–897.

Chemical Abstracts, vol. 81, No. 13, Sep. 30, 1974, Columbus Ohio, US; abstract No. 78113, XP002068295; see abstract & J.E. McMurry et al.: Journal of the American Chemical Society, vol. 96, No. 14, 1974, DC US, pp. 4708–4709.

Chemical Abstracts, vol. 97, No. 5, Aug. 2, 1982, Columbus Ohio, US; abstract No. 38616, XP002068296; see abstract & A. Clerici et al.: J. Org. Chem., vol. 47, No. 15, 1982, pp. 2852–2856.

Chemical Abstracts, vol. 96, No. 5, Feb. 1, 1982, Columbus Ohio, US; abstract No. 34276, XP00206897; see abstract & R. Dams et al.: J. Org. Chem., vol. 47, No. 2, 1982, pp. 248–259.

*Primary Examiner*—Fiona T. Powers
*Attorney, Agent, or Firm*—Karen Lee Orzechowski

[57] ABSTRACT

5,6-Dihydro-11H-dibenzo[a,d]cyclohept-11-enes are prepared by reacting a dibenzosuberone or an aza derivative thereof with an aliphatic ketone in the presence of low valent titanium.

17 Claims, No Drawings

PROCESS FOR THE PREPARATION OF 10, 11-DIHYDRO-5H-DIBENZO[A,D] CYCLOHEPT-5-ENES AND DERIVATIVES THEREOF

The present invention relates to a process for the preparation of 10,11-dihydro-5H-dibenzo[a,d]cyclohept-5-enes such as loratadine.

The anti-histamine ethyl 4-(8-chloro-5,6-dihydro-11H-benzo[5,6]cyclohepta[1,2-b]pyridin-11-ylidene) piperidine-1-carboxylate (loratadine) is a potent, long acting derivative of azatadine which shows negligible CNS side effects.

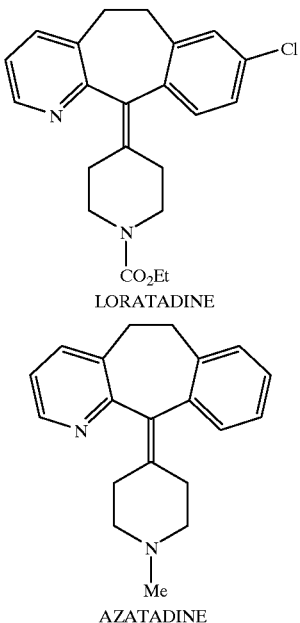

LORATADINE

AZATADINE

The presence of the chlorine atom at the 8-position makes the chemistry of loratadine uniquely problematical and reductive preparations are ineffective because of the removal of chlorine at the 8-position.

U.S. Pat. No. 3,326,924 (Villani et al) discloses processes for preparing various aza-dibenzo[a,d]-cycloheptene derivatives which involve production of a tricyclic ketone which is reacted with a Grignard reagent derived from 4-chloro-N-methyl piperidine. Dehydration gives the N-methyl product. The process is, however, hindered by the amount up to 30% of 1,6-addition product which is generated in the Grignard reaction causing problems in yield and purification. U.S. Pat. No. 4,282,233 (Villani) discloses the preparation of loratadine from the product of the above reaction by demethylation/carboethoxylation.

A synthetic route to loratadine is disclosed in U.S. Pat. No. 4,659,716 (Villani et al), U.S. Pat. No. 4,731,447 (Schumacher et al), U.S. Pat. No. 4,873,335 (Schumacher et al) and Journal of organic Chemistry, 1989, Vol 54,2242–2244 (Schumacher et al.) which involves alkylation of the dianion of the t-butylamide of 2-cyano-3-methyl-pyridine, re-generation of the nitrile, Grignard reaction, cyclisation with $HF/BF_3$ and demethylation/carboethoxylation. This process is, however, hampered by the need to use hazardous organometallic reagents (LDA or butyl lithium) and a super-acid environment of liquid HF and $BF_3$ gas.

Cid et al have reported (Tetrahedron, 1988, Vol 44, 6197–6200) that cross coupling reactions between a tricyclic ketone and a cyclic ketone can take place using low valent titanium to give biphenylmethylene piperidines or cyproheptadine. The process suffers from the disadvantages that low valent titanium has to be generated using lithium metal which is hazardous on industrial scale and by the need to use about 12 equivalents of titanium reagent to prevent the reaction stopping at the diol stage.

In general there exists a need for improved processes for preparing 10,11-dihydro-5H-dibenzo[a,d]-cycloheptenes which use less hazardous materials and provide improved yields and selectivity, particularly on industrial scale production. The present invention seeks to provide such an improved process.

It has now surprisingly been found that hetero-coupling of a tricyclic aromatic ketone with an aliphatic cyclic ketone in the presence of low valent titanium gives a high yield of unsaturated coupled product with only traces of homo-coupled ketones. Typically, the low valent titanium is present as titanium (II) And only a slight excess of titanium reagent is required.

Thus viewed from one aspect the present invention provides a process for preparing 5,6-dihydro-11H-dibenzo[a,d]cyclohept-11-enes comprising reacting a dibenzosuberone or an aza derivative thereof with an aliphatic ketone in the presence of low valent titanium, ie. Ti(O), Ti(I) or Ti(II) wherein said low valent titanium is generated by zinc. Preferably the low valent titanium consists essentially of Ti(II).

Preferably the dibenzosuberone or aza derivative thereof compound is of formula I:

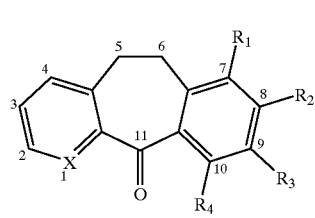

(I)

(wherein:
  X denotes nitrogen or CH;
  and $R^1$, $R^2$, $R^3$ and $R^4$ which may be the same or different independently denote hydrogen or a halogen (eg. F, Cl or Br)).

Preferably the dibenzosuberone compound is one in which $R^2$ denotes a halogen (eg. chloro) and $R^1$, $R^3$ and $R^4$ denote hydrogen and particularly preferably in which in addition X is nitrogen.

In further embodiments, X which is nitrogen may be at the 2, 3 or 4 position as defined in formula I.

Preferably the aliphatic ketone is cyclic and particularly preferably is an optionally N-substituted piperidone compound, for example a compound of formula II:

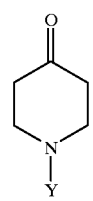

(wherein:
  Y denotes hydrogen, lower alkyl (eg $C_{1-6}$-alkyl), $CO_2R^5$, $SO_2R^5$, $CON(R^5)_2$, $SO_2N(R^5)_2$, $CO_2COR^5$ or a N-protecting group; and
  $R^5$ is hydrogen, a $C_{1-12}$-alkyl (preferably $C_{1-6}$-alkyl) group optionally substituted by one or more amino or $C_{1-6}$-alkylamino groups, a phenyl group optionally substituted by one or more halo or $C_{1-6}$-alkyl groups, a $C_{7-12}$-phenylalkyl group optionally substituted at the phenyl by one or more halo or $C_{1-6}$-alkyl groups, 2-piperidyl, 3-piperidyl or piperidyl substituted at the nitrogen atom by a $C_{1-4}$-alkyl group);
and the salts thereof.

Preferably the piperidone is one in which Y is the group $CO_2Et$.

The reaction proceeds via an intermediate diol which, if desired, may be isolated by conducting the reaction at a lower temperature. The olefin may be prepared from the intermediate diol in a subsequent step in a conventional manner.

The diol intermediate itself is novel and forms a further aspect of the invention. Thus the present invention provides a compound of formula III:

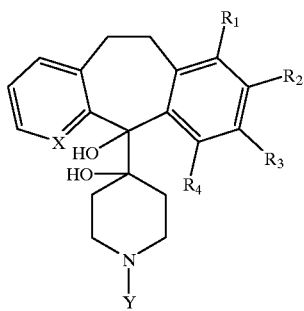

(III)

(wherein $R_1$, $R_2$, $R_3$, $R_4$, X are Y are as defined hereinbefore).

The preferred compound is:

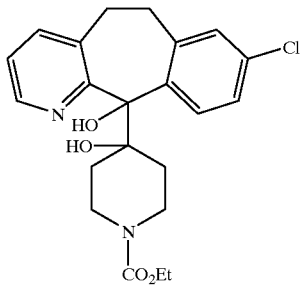

The dibenzosuberone and aliphatic ketone reagents are preferably reacted in substantially equimolar quantities; however an excess of either reagent can be tolerated, eg. the two reagents may be present in molar ratios of from 1:2 to 2:1, preferably 1.5:1 to 1:1.5, especially preferably 1.1:1 to 1:1.1.

Low valent titanium may be prepared in situ, using zinc eg. by reaction of a Ti (III) or Ti (IV) compound or complexes thereof with zinc. In one preferred embodiment of the method according to the invention, a combination of titanium (IV) chloride or a complex thereof and zinc is used to generate low talent titanium. This embodiment has the advantage that zinc is relatively cheap and safe to use on an industrial scale. A combination of titanium (III) chloride and zinc may be used with equal success.

In accordance with the invention, Zn and Ti may be conveniently used in molar ratios of 4:1 to 1:1, preferably 3:1 to 2:1.

Typically, a slight molar excess of titanium reagent is used over the amount of ketone present, although a larger excess may be used if desired.

The titanium reagent is preferably used at a molar ratio of from 0.5:1 to 6:1, preferably 1.5:1 to 4:1, particularly 2:1 to 3:1 relative to the dibenzosuberone.

The reaction may be conveniently conducted in etherial solvents such as for example tetrahydrofuran, dioxane and dimethoxyethane which are commonly used in coupling reactions involving titanium. Nevertheless ethyl acetate, iso-propyl acetate, t-butylacetate, DMF and acetonitrile are equally effective for this purpose. Tetrahydrofuran is preferred.

The reaction temperature may be conveniently in the range −10° C. to the reflux temperature of the chosen solvent, but is preferably 100° C. or less, especially 20 to 60° C. To prepare the diol the reaction temperature is preferably below 10° C.

As noted above, Y may represent an N-protecting group and suitable groups includes acetyl, benzoyl, ethoxycarbonyl, t-butoxycarbonyl, benzyloxycarbonyl, benzyl, methoxy benzyl or 2,4-methoxybenzyl groups. The optional subsequent cleavage of a N-protecting group may for example be carried out by conventional means eg. hydrolytically, hydrogenolytically or in the presence of an oxidising agent or acid. Further examples of N-protecting groups and appropriate deprotection reactions are described in the literature (see for example McOmie, "Protecting groups in organic chemistry", Plenum, 1973 and Greene, "Protective groups in organic synthesis", Wiley Interscience 1981).

The process according to the invention is typically carried out at elevated temperature (eg. under reflux) for at least one hour, preferably 1–4 hours, particularly preferably 1–2 hours and at ambient pressure.

The process according to the invention provides a yield of a 10,11-dihydro-5H-dibenzo[a,d]cyclo-heptene typically in excess of 60% and often 80% or more.

The invention is illustrated in a non-limiting fashion by the following examples in which all ratios and percentages are by weight unless otherwise stated:

EXAMPLE 1

Preparation of ethyl 4-(5,6-dihydro-11H-benzo[5,6]cycloheptan)-piperylidene-1-carboxylate A mixture of 4-carboethoxypiperidone (5.64 g, 33 mmole) and dibenzosuberone (6.24 g, 30 mmole) are dissolved in tetrahydrofuran (82 ml) under a nitrogen atmosphere. Zinc (8.83 g, 135 mmole) is added and the mixture cooled to 0° C. Titanium tetrachloride (7.4 ml, 67.5 mmole) is added over 15 minutes so that the temperature does not exceed 30° C. The mixture is then heated at reflux for about 1.5 hours.

About 50 ml of THF is removed by distillation under reduced pressure and the residue is partitioned between toluene (100 ml) and 2M HCl (100 ml). The layers are separated and the aqueous phase extracted with a further 100 ml toluene. The combined organic phase is washed with 50 ml 10% potassium carbonate solution and dried over magnesium sulphate.

Removal of the solvent and chromatography of the residue (10.3 g) on silica gel using ether:dichloromethane (5:95) gives 9.3 g (89%) product at constant weight as a viscous oil which crystallises on standing to give a solid (MP 87–90° C.).

EXAMPLE 2

Preparation of ethyl 4-(5,6-dihydro-11H-benzo[5,6]cycloheptan)-piperylidene-1-carboxylate A mixture of-4-carboethoxypiperidone (3.8 g, 22 mmole) and dibenzosuberone (4.4 g, 20 mmole) are dissolved in ethyl acetate (50 ml). Zinc (6.4 g, 100 mmole) is added and the mixture cooled to 0° C. Titanium tetrachloride (4.9 ml, 45 mmole) is added over about 5 minutes so that the temperature stays below 15° C. (If required, the diol may be isolated at this stage by addition to water.) The reaction is heated to reflux for 2 hours. The mixture is allowed to cool and 75 ml 2M HCl is added. The aqueous phase is extracted with a further 50 ml ethyl acetate. The combined organic phase is washed with 50 ml 10% potassium carbonate solution and dried over magnesium sulphate.

The solvent is removed to constant weight under vacuum to give 6.8 g crude product which is contaminated with a small amount of deoxygenated tricycle.

EXAMPLE 3

Preparation of Loratadine

8-Chloro-5,6-dihydro-11H-benzo[5,6]cyclohepta[1,2-b]pyridin-11-one (2.45 g, 10 mmole) (see J. Heterocyclic Compounds, vol. 8, 1971, page 73) and 4-carboethoxypiperidone (1.8 g, 10 mmole) are dissolved in 30 ml tetrahydrofuran. Zinc (5 g, 78 mmole) is added and the mixture cooled to 0° C. Titanium tetrachloride (3 ml, 27 mmole) is added over about 10 minutes. The mixture is then heated at reflux for 1 hour. The mixture is added to 100 ml water and 50 ml toluene. Most of the aqueous phase is separated and the organic phase is washed with 20 ml ammonium hydroxide solution.

The mixture is filtered through celite and the celite washed with a further 50 ml toluene. The organic phase is separated and dried over magnesium sulphate.

The solvent is removed and the residue (3.75 g) is crystallised from butyl ether to give 2.5 g loratadine (68%). HPLC shows the product to be >98% pure.

What is claimed is:

1. A process for preparing 5,6-dihydro-11H-dibenzo[a,d]cyclohept-11-enes comprising reacting a dibenzosuberone or an aza derivative thereof with an aliphatic ketone in the presence of low valent titanium wherein said low valent titanium is generated by zinc.

2. A process as claimed in claim 1 wherein said dibenzosuberone or aza derivative thereof is of formula I:

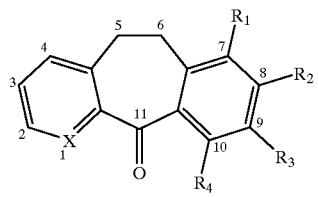

wherein:

X denotes nitrogen or CH;

and $R^1$, $R^2$, $R^3$ and $R^4$ which may be the same or different independently denote hydrogen or a halogen.

3. A process as claimed in claim 2 wherein $R^2$ is a halogen.

4. A process as claimed in claim 2 wherein $R^1$, $R^3$ and $R^4$ denote hydrogen.

5. A process as claimed in claim 2 wherein X is nitrogen.

6. A process as claimed in claim 1 in which the aliphatic ketone is cyclic.

7. A process as claimed in claim 6 wherein said cyclic aliphatic ketone is an optionally N-substituted piperidone.

8. A process as claimed in claim 7 wherein said piperidone is of formula II:

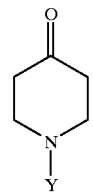

(wherein:

Y denotes hydrogen, lower alkyl, $CO_2R^5$, $SO_2R^5$, $CON(R^5)_2$, $SO_2N(R^5)_2$, $CO_2COR^5$ or a N-protecting group; and $R^5$ is hydrogen, a $C_{1-12}$-alkyl group optionally substituted by one or more amino or $C_{1-6}$-alkylamino groups, a phenyl group optionally substituted by one or more halo or $C_{1-6}$-alkyl groups, a $C_{7-12}$-phenylalkyl group optionally substituted at the phenyl by one or more halo or $C_{1-6}$-alkyl groups, 2-piperidyl, 3-piperidyl or piperidyl substituted at the nitrogen atom by a $C_{1-4}$-alkyl group)

and the salts thereof.

9. A process as claimed in claim 8 wherein Y is $CO_2Et$.

10. A process as claimed in claim 1 wherein Ti is present in a molar ratio range 1.5:1 to 4:1 relative to the dibenzosuberone.

11. A process as claimed in claim 10 wherein Ti is present in a molar ratio range 2:1 to 3:1 relative to the dibenzosuberone.

12. A process as claimed in claim 1 comprising the preparation of an intermediate diol of formula III:

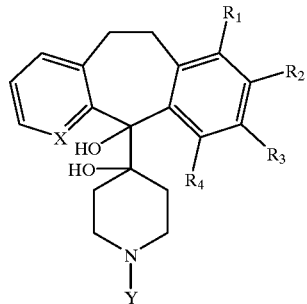

wherein X denotes nitrogen or CH:

and $R^1$, $R^2$, $R^3$ and $R^4$ which may be the same or different independently denote hydrogen or a halogen Y denotes hydrogen, lower alkyl, $CO_2R^5$, $SO_2R^5$, $CON(^5)_2$, $SO_2N(R^5)_2$, $CO_2COR^5$ or a N-protecting group; and $R^5$ is hydrogen, a $C_{1-12}$-alkyl group optionally substituted by one or more amino or $C_{1-6}$-alkylamino groups, a phenyl group optionally substituted by one or more halo or $C_{1-6}$-alkyl groups, a $C_{7-12}$-phenylalkyl group optionally substituted at the phenyl by one or more halo $C_{1-6}$-alkyl groups, 2-piperidyl, 3-piperidyl or piperidyl substituted at the nitrogen atom by a $C_{1-4}$-alkyl group.

13. A process as claimed in claim 1 wherein said low valent titanium consists essentially of Ti (II).

14. A process as claimed in claim 1 wherein low valent titanium is prepared in situ.

15. A process as claimed in claim 14 wherein low valent titanium is prepared by reacting a Ti(III) or Ti(IV) compound or complex with said zinc.

16. A process as claimed in claim 15 wherein said titanium compound is titanium(III) chloride or titanium(IV) chloride or a complex thereof.

17. A process as claimed in claim 1 for preparing Loratadine.

* * * * *